United States Patent [19]

Palmer

[11] Patent Number: 5,270,305
[45] Date of Patent: * Dec. 14, 1993

[54] MEDICAMENTS

[75] Inventor: James B. D. Palmer, Greenford, United Kingdom

[73] Assignee: Glaxo Group Limited, London, United Kingdom

[*] Notice: The portion of the term of this patent subsequent to May 4, 2010 has been disclaimed.

[21] Appl. No.: 753,907

[22] Filed: Sep. 3, 1991

Related U.S. Application Data

[63] Continuation of Ser. No. 578,601, Sep. 7, 1990, abandoned.

[30] Foreign Application Priority Data

Sep. 8, 1989 [GB] United Kingdom ............ 8920392.1
Oct. 20, 1989 [GB] United Kingdom ............ 8923644.2

[51] Int. Cl.$^5$ ..................... A61K 31/59; A61K 9/14
[52] U.S. Cl. ..................................................... 514/171
[58] Field of Search ................................. 514/170, 171

[56] References Cited

U.S. PATENT DOCUMENTS

| | | | |
|---|---|---|---|
| 4,278,673 | 7/1981 | Hartley et al. | 514/243 |
| 4,335,121 | 6/1982 | Phillips et al. | 514/179 |
| 4,513,001 | 4/1985 | Joannic et al. | 514/394 |
| 4,778,054 | 10/1988 | Newell et al. | 206/531 |
| 4,811,731 | 3/1989 | Newell et al. | 428/203.15 |
| 4,814,161 | 3/1989 | Jinks et al. | 424/45 |
| 4,866,051 | 9/1989 | Hunt et al. | 514/180 |
| 4,906,476 | 3/1990 | Raedaakkishinan | 424/450 |
| 4,985,418 | 1/1991 | Richards | 514/174 |

FOREIGN PATENT DOCUMENTS

| | | | |
|---|---|---|---|
| 2107715 | 5/1983 | United Kingdom | 514/170 |
| 2140800 | 12/1984 | United Kingdom | |
| 2187953 | 9/1987 | United Kingdom | 514/170 |
| WO87/05213 | 9/1987 | World Int. Prop. O. | |

OTHER PUBLICATIONS

ABPI Data Sheet Compendium 1989–1990 (published Apr. 1989).
Jeppson et al. CA. 110:147583r (1989).

*Primary Examiner*—Shep K. Rose
*Attorney, Agent, or Firm*—Bacon & Thomas

[57] ABSTRACT

Pharmaceutical compositions comprising effective amounts of salmeterol (and/or a physiologically acceptable salt thereof) and fluticasone propionate as a combined preparation for simultaneous, sequential or separate administration by inhalation in the treatment of respiratory disorders.

11 Claims, No Drawings

MEDICAMENTS

This application is a continuation of U.S. patent application Ser. No. 07/578,601, filed Sept. 7, 1990.

This invention relates to improvements in the treatment of asthma and other respiratory disorders. More particularly, it relates to the use of a bronchodilator drug in combination with a steroidal anti-inflammatory drug for the treatment of respiratory disorders such as asthma, and to pharmaceutical compositions containing the two active ingredients.

Asthma is a condition characterised by variable, reversible obstruction of the airways which is caused by a complex inflammatory process within the lungs. In most cases, this process is initiated and maintained by the inhalation of antigens by sensitive atopic individuals (extrinsic asthma). However, in some patients it is caused by other mechanisms which at present are poorly understood but do not involve an allergic process (intrinsic asthma). The disease has therefore two components, spasm of the bronchial (or breathing) tubes and inflammation or swelling of the breathing tubes.

Salbutamol, the first highly selective $\beta_2$-adrenoceptor stimulant has been used successfully and effectively by inhalation for the immediate relief of spasm in asthma. However, when given by inhalation, salbutamol has usually a four to six hour duration of action, which is too short either to control nocturnal asthma or for convenient maintenance of the disease in some patients.

Anti-inflammatory corticosteroids such as, for example, beclomethasone dipropionate have also been administered by inhalation in the treatment of asthma, although unlike salbutamol the therapeutic benefits resulting from reduced inflammation may not be immediately apparent.

It has been recognized that asthma may be treated by using both a bronchodilator for immediate relief and a prophylactic anti-inflammatory corticosteroid to treat the underlying inflammation. Such combination therapy directed at the two main underlying events in the lung (i.e. relief of spasm in the breathing tubes and treatment of inflammation in the breathing tubes) using a combination of salbutamol and beclomethasone dipropionate has previously been proposed (Ventide, Glaxo Group trade mark), but suffers a number of disadvantages in view of the above-mentioned short duration of action exhibited by salbutamol. Thus the need for a 4-hourly dosing regimen may discourage effective patient compliance and also renders the product less than satisfactory in the treatment of nocturnal asthma since the bronchodilator may not remain effective for the duration of the night, leading to impaired sleep for asthmatics troubled by nocturnal cough, breathlessness and wheeze.

The present invention is based on the concept of a novel combination therapy which has markedly greater efficiency and duration of bronchodilator action than previously known combinations and which permits the establishment of a twice daily (bis in diem—b.i.d) dosing regimen with consequent substantial benefits in, for example, the treatment of asthma, particularly nocturnal asthma.

Thus we have found that if the $\beta_2$-adrenoreceptor stimulant brochodilator salmeterol and/or a physiologically acceptable salt thereof is combined with the anti-inflammatory corticosteroid fluticasone propionate in a form suitable for administration by inhalation, the resulting compositions may be administered on a b.i.d. basis to provide highly effective treatment and/or prophylactic therapy for asthmatics. In particular such administration has been shown to lead to significant improvement in daytime lung function, requirement for additional symptomatic bronchodilator and almost complete abolition of nocturnal asthma while giving rise to minimal systemic side effects.

Salmeterol is one of a range of bronchodilators having extended duration of action which is described in British Patent Specification No. 2140800, and is systematically named 4-hydroxy-$\alpha^1$-[[[6-(4-phenylbutoxy)hexyl]amino]methyl]-1,3-benzenedimethanol. Fluticasone propionate is one of a range of topical anti-inflammatory corticosteroids with minimal liability to undesired systemic side effects which is described in British Patent Specification No. 2088877, and is systematically named S-fluoromethyl 6$\alpha$,9$\alpha$-difluoro-11$\beta$-hydroxy-16$\beta$-methyl-17$\alpha$-propionyloxy -3-oxoandros-1,4-diene-17$\beta$-carbothioate. We have found these two compounds to be particularly compatible and complementary in their activity and thus highly effective in the treatment of asthma and other respiratory disorders.

Thus according to one aspect of the invention there are provided pharmaceutical compositions comprising effective amounts of salmeterol (and/or a physiologically acceptable salt thereof) and fluticasone propionate as a combined preparation for simultaneous, sequential or separate administration by inhalation in the treatment of respiratory disorders.

The invention additionally relates to the use of salmeterol (and/or a physiologically acceptable salt thereof) and fluticasone propionate in the manufacture of pharmaceutical compositions as combined preparations for simultaneous, sequential or separate administration of salmeterol and fluticasone propionate by inhalation in the treatment of respiratory disorders.

According to a further feature of the invention there is provided a method of treating respiratory disorders which comprises the simultaneous, sequential or separate administration by inhalation of effective amounts of salmeterol (and/or a physiologically acceptable salt thereof) and fluticasone propionate.

Suitable physiologically acceptable salts of salmeterol include acid addition salts derived from inorganic and organic acids, such as the hydrochloride, hydrobromide, sulphate, phosphate, maleate, tartrate, citrate, benzoate, 4-methoxybenzoate, 2- or 4-hydroxybenzoate, 4-chlorobenzoate, p-toluenesulphonate, methanesulphonate, ascorbate, salicylate, acetate, fumarate, succinate, lactate, glutarate, gluconate, tricarballylate, hydroxynaphthalenecarboxylate e.g. 1-hydroxy- or 3-hydroxy-2-naphthalenecarboxylate, or oleate. Salmeterol is preferably used in the form of its 1-hydroxy-2-naphthalene carboxylate salt (hydroxynaphthoate).

For administration by inhalation, the compositions according to the invention are conveniently delivered by conventional means, e.g. in the form of a metered dose inhaler prepared in a conventional manner or in combination with a spacer device such as the Volumatic (Glaxo Group trade mark) device. In the case of a metered dose inhaler, a metering valve is provided to deliver a metered amount of the composition. Spray compositions may for example be formulated as aqueous solutions or suspensions and may be administered by a nebuliser. Aerosol spray formulations, for example in which the active ingredients are suspended, optionally together with one or more stabilisers, in a propellant, e.g. a halogenated hydrocarbon such as trichlorofluoromethane, dichlorodifluoromethane, 1,2-dichlorotetrafluoroethane, trichlorotrifluoroethane, monochloropentafluoroethane, chloroform or methylene chloride, may also be employed. The two drugs may be administered separately in similar ways.

Alternatively, for administration by inhalation or insufflation, the compositions according to the invention may take the form of a dry powder composition, for example a powder mix of the active ingredients and a suitable carrier such as lactose. The powder compositions may be presented in unit dosage form in, for example, capsules, cartridges or blister packs from which the powder may be administered with the aid of an inhaler such as the Rotahaler inhaler (Glaxo Group trade mark) or in the case of blister packs by means of the Diskhaler inhaler (Glaxo Group trade mark).

The ratio of salmeterol to fluticasone propionate in the compositions according to the invention is preferably within the range 4:1 to 1:20. The two drugs may be administered separately in the same ratio. Each metered dose or actuation of the inhaler will generally contain from 25 μg to 100 μg of salmeterol and from 25 μg to 500 μg of fluticasone propionate. As hereinbefore indicated, it is intended that the pharmaceutical compositions will be administered twice daily.

A suitable daily dose of salmeterol for inhalation is in the range 50 μg to 200 μg.

A suitable daily dose of fluticasone propionate for inhalation is in the range 50 μg to 2000 μg depending on the severity of the disease.

The precise dose employed will of course depend on the method of administration, the age, weight and condition of the patient and will be determined by the clinician depending on the severity and the type of asthma.

In order that the invention may be more fully understood, the following examples are given by way of illustration only.

EXAMPLE 1

Metered Dose Inhaler

| Active Ingredient | Target per Actuation | Per Inhaler % w/w |
| --- | --- | --- |
| Salmeterol (as hydroxynaphthoate) | 25.0 μg | 0.0448 |
| Fluticasone propionate | 25.0 μg | 0.0309 |
| Stabiliser | 5.0 μg | 0.0076 |
| Trichlorofluoromethane | 23.70 mg | 27.8759 |
| Dichlorodifluoromethane | 61.25 mg | 72.0588 |

EXAMPLE 2

Metered Dose Inhaler

| Active Ingredient | Target per Actuation | Per Inhaler % w/w |
| --- | --- | --- |
| Salmeterol (as hydroxynaphthoate) | 25.0 μg | 0.0448 |
| Fluticasone propionate | 50.0 μg | 0.0618 |
| Stabiliser | 7.5 μg | 0.0106 |
| Trichlorofluoromethane | 23.67 mg | 27.8240 |
| Dichlorodifluoromethane | 61.25 mg | 72.0588 |

EXAMPLE 3

Metered Dose Inhaler

| Active Ingredient | Target per Actuation | Per Inhaler % w/w |
| --- | --- | --- |
| Salmeterol (as hydroxynaphthoate) | 25.0 μg | 0.0448 |
| Fluticasone propionate | 250.0 μg | 0.3088 |
| Stabiliser | 25.0 μg | 0.0309 |
| Trichlorofluoromethane | 23.45 mg | 27.5567 |
| Dichlorodifluoromethane | 61.25 mg | 72.0588 |

EXAMPLE 4

Metered Dose Inhaler

| Active Ingredient | Target per Actuation | Per Inhaler % w/w |
| --- | --- | --- |
| Salmeterol (as hydroxynaphthoate) | 25.0 μg | 0.0448 |
| Fluticasone propionate | 125.0 μg | 0.1544 |
| Stabiliser | 15.0 μg | 0.0175 |
| Trichlorofluoromethane | 23.56 mg | 27.7244 |
| Dichlorodifluoromethane | 61.25 mg | 72.0588 |

EXAMPLE 5

Metered Dose Inhaler

| Active Ingredient | Target per Actuation | Per Inhaler % w/w |
| --- | --- | --- |
| Salmeterol (as hydroxynaphthoate) | 100.0 μg | 0.1791 |
| Fluticasone propionate | 250.0 μg | 0.3088 |
| Stabiliser | 25.0 μg | 0.0309 |
| Trichlorofluoromethane | 23.43 mg | 27.4224 |
| Dichlorodifluoromethane | 61.25 mg | 72.0588 |

In Examples 1 to 5 micronised fluticasone propionate and micronised salmeterol (as the hydroxynaphthoate) are added in the proportions given above either dry or after predispersal in a small quantity of stabiliser (disodium dioctylsulphosuccinate, lecithin, oleic acid or sorbitan trioleate)/trichlorofluoromethane solution to a suspension vessel containing the main bulk of the trichlorofluoromethane solution. The resulting suspension is further dispersed by an appropriate mixing system using, for example, a high shear blender, ultrasonics or a microfluidiser until an ultrafine dispersion is created. The suspension is then continuously recirculated to suitable filling equipment designed for cold fill or pressure filling of dichlorodifluoromethane. Alternatively, the suspension may be prepared in a suitable chilled solution of stabiliser, in trichlorofluoromethane/ dichlorodifluoromethane.

EXAMPLE 6

Metered Dose Dry Powder Formulation

| Active Ingredient | | μg/cartridge or blister |
| --- | --- | --- |
| Salmeterol (as hydroxynaphthoate) | | 36.3 |
| Fluticasone propionate | | 50.00 |
| Lactose Ph. Eur. | to | 12.5 mg or |
| | to | 25.0 mg |

EXAMPLE 7

Metered Dose Dry Powder Formulation

| Active Ingredient | μg/cartridge or blister |
|---|---|
| Salmeterol (as hydroxynaphthoate) | 72.5 |
| Fluticasone propionate | 50.00 |
| Lactose Ph. Eur. | to 12.5 mg or to 25.0 mg |

EXAMPLE 8

Metered Dose Dry Powder Formulation

| Active Ingredient | μg/cartridge or blister |
|---|---|
| Salmeterol (as hydroxynaphthoate) | 72.5 |
| Fluticasone propionate | 100.00 |
| Lactose Ph. Eur. | to 12.5 mg or to 25.0 mg |

EXAMPLE 9

Metered Dose Dry Powder Formulation

| Active Ingredient | μg/cartridge or blister |
|---|---|
| Salmeterol (as hydroxynaphthoate) | 72.5 |
| Fluticasone propionate | 250 |
| Lactose Ph. Eur. | to 12.5 mg or to 25.0 mg |

EXAMPLE 10

Metered Dose Dry Powder Formulation

| Active Ingredient | μg/cartridge or blister |
|---|---|
| Salmeterol (as hydroxynaphthoate) | 72.5 |
| Fluticasone propionate | 500.0 |
| Lactose Ph. Eur. | to 12.5 mg or to 25.0 mg |

EXAMPLE 11

Metered Dose Dry Powder Formulation

| Active Ingredient | μg/cartridge or blister |
|---|---|
| Salmeterol (as hydroxynaphthoate) | 145.0 |
| Fluticasone propionate | 250.0 |
| Lactose Ph. Eur. | to 12.5 mg or to 25.0 mg |

In Examples 6 to 11 the active ingredients are micronised and bulk blended with the lactose in the proportions given above. The blend is filled into hard gelatin capsules or cartridges or in specifically constructed double foil blister packs (Rotadisks blister packs, Glaxo Group trade mark) to be administered by an inhaler such as the Rotahaler inhaler (Glaxo Group trade mark) or in the case of the blister packs with the Diskhaler inhaler (Glaxo Group trade mark).

I claim:

1. A pharmaceutical composition comprising effective amounts of salmeterol or a physiologically acceptable salt thereof and fluticasone propionate as a combined preparation for simultaneous, sequential or separate administration by inhalation in the treatment of respiratory disorders.

2. A composition as claimed in claim 1 wherein salmeterol is present as its 1-hydroxy-2-naphthalenecarboxylate salt.

3. A composition as claimed in claim 1 presented in the form of a metered dose inhaler or a metered dry powder composition.

4. A composition as claimed in claim 1 in dosage unit form comprising 25-100 μg of salmeterol or a physiologically acceptable salt thereof and 25-500 μg of fluticasone propionate per dosage unit.

5. A composition as claimed in claim 2 presented in the form of a metered dose inhaler or a metered dry powder composition.

6. A composition as claimed in claim 2 in dosage unit form comprising 25-100 μg of the 1-hydroxy-2-naphthalenecarboxylate salt of salmeterol and 25-500 μg of fluticasone propionate per dosage unit.

7. A composition as claimed in claim 6 presented in the form of a metered dose inhaler or a metered dry powder composition.

8. The use of salmeterol or a physiologically acceptable salt thereof and fluticasone propionate in the manufacture of pharmaceutical compositions as combined preparations for simultaneous, sequential or separate administration of salmeterol and fluticasone propionate by inhalation in the treatment of respiratory disorders.

9. A method of treating respiratory disorders which comprises the simultaneous, sequential or separate administration by inhalation of effective amounts of salmeterol or a physiologically acceptable salt thereof and fluticasone propionate.

10. A method as claimed in claim 9 wherein the salmeterol or a physiologically acceptable salt thereof and the fluticasone propionate are administered on a twice daily basis.

11. A method as claimed in claim 10 wherein the effective amount of salmeterol or a physiologically acceptable salt thereof is 50-200 μg per day and the effective amount of fluticasone propionate is 50-1000 μg per day.

* * * * *

UNITED STATES PATENT AND TRADEMARK OFFICE
CERTIFICATE OF CORRECTION

PATENT NO. : 5,270,305
DATED : December 14, 1993
INVENTOR(S) : PALMER

It is certified that error appears in the above-indentified patent and that said Letters Patent is hereby corrected as shown below:

Item [*] should read as follows:

[*] Notice: The portion of the term of this patent subsequent to September 7, 2010 has been disclaimed.

Signed and Sealed this

Seventeenth Day of April, 2001

Attest:

NICHOLAS P. GODICI

Attesting Officer     Acting Director of the United States Patent and Trademark Office